United States Patent [19]

Henkelmann et al.

[11] Patent Number: 5,639,890

[45] Date of Patent: Jun. 17, 1997

[54] PREPARATION OF N-AKENYLCARBAMIC ESTERS

[75] Inventors: Jochem Henkelmann, Mannheim; Marc Heider, Neustadt; Thomas Rühl, Frankenthal, all of Germany

[73] Assignee: BASF Aktiengesellschaft, Ludwigshafen, Germany

[21] Appl. No.: 705,682

[22] Filed: Aug. 29, 1996

[30] Foreign Application Priority Data

Sep. 8, 1995 [DE] Germany .................. 195 33 219.9

[51] Int. Cl.[6] .................................. C07D 263/14
[52] U.S. Cl. ........................... 548/231; 560/157
[58] Field of Search ................. 548/231; 560/157

[56] References Cited

U.S. PATENT DOCUMENTS

| | | | |
|---|---|---|---|
| 3,579,515 | 5/1971 | Walles | 260/244 |
| 4,680,410 | 7/1987 | Wang | 548/231 |
| 4,831,153 | 5/1989 | Phung | 548/231 |
| 5,155,253 | 10/1992 | Murray | 560/225 |
| 5,233,077 | 8/1993 | Waller | 560/157 |

FOREIGN PATENT DOCUMENTS

| | | | |
|---|---|---|---|
| 351603 | 1/1990 | European Pat. Off. | 560/157 |
| 703219 | 3/1996 | European Pat. Off. | 548/231 |
| 851773 | 10/1960 | United Kingdom | 560/157 |

OTHER PUBLICATIONS

"Beilsteins Handbuch Der Organischen Chemie", 1979, XP002019733, vol. 4, 4., pp. 1054–1055.
"Beilsteins Handbuch Der Organischen Chemie", 1978, XP002019666, vol. 6, 4., p. 631.
CA 76:60136c Synthesis, . . . –Oxazolidone, Culbertson et al., p. 5, 1972.
CA 113:39951n Transvinylation . . . acids. Murray, p. 549, 1990.

*Primary Examiner*—Joseph McKane
*Attorney, Agent, or Firm*—Keil & Weinkauf

[57] ABSTRACT

N-Alkenylcarbamic esters of the general formula I $$HR^1C=CR^1-\underset{\underset{R^2}{|}}{N}-\underset{\underset{O}{\|}}{C}-O-R^3 \qquad \text{I}$$

where at least one of the $R^1$ radicals is hydrogen and the second $R^1$ radical is hydrogen or $C_1$–$C_4$—alkyl, the $R^2$ radical is an aliphatic, cycloaliphatic, araliphatic or aromatic radical which can be linked to the $R^3$ radical to form a 2- to 10-membered bridge, and the $R^3$ radical is an aliphatic, cycloaliphatic or aromatic radical, from an alkenyl carboxylate of the general formula II $$HR^1C=CR^1-O-\underset{\underset{O}{\|}}{C}-R^4 \qquad \text{II}$$

where $R^1$ has the abovementioned meaning, and $R^4$ is hydrogen, an aliphatic, cycloaliphatic or aromatic radical, and a carbamic ester of the general formula III $$HR^2N-\underset{\underset{O}{\|}}{C}-O-R^3 \qquad \text{III}$$

where the $R^2$ and $R^3$ radicals have the abovementioned meanings, are prepared by reacting the starting compounds in the presence of a base.

9 Claims, No Drawings

PREPARATION OF N-AKENYLCARBAMIC ESTERS

The present invention relates to a novel process for preparing N-alkenylcarbamic esters of the general formula I $$HR^1C=CR^1-\underset{R^2}{N}-\underset{\underset{O}{\|}}{C}-O-R^3 \quad \text{I}$$

where at least one of the $R^1$ radicals is hydrogen and the second $R^1$ radical is hydrogen or $C_1$-$C_4$—alkyl, the $R^2$ radical is an aliphatic, cycloaliphatic, araliphatic or aromatic radical which can be linked to the $R^3$ radical to form a 2- to 10-membered bridge, and the $R^3$ radical is an aliphatic, cycloaliphatic or aromatic radical, from an alkenyl carboxylate of the general formula II $$HR^1C=CR^1-O-\underset{\underset{O}{\|}}{C}-R^4 \quad \text{II}$$

where $R^1$ has the abovementioned meaning, and $R^4$ is hydrogen, an aliphatic, cycloaliphatic or aromatic radical, and a carbamic ester of the general formula III $$HR^2N-\underset{\underset{O}{\|}}{C}-O-R^3 \quad \text{III}$$

where the $R^2$ and $R^3$ radicals have the abovementioned meanings.

The products of the formula I are intermediates which are in demand for synthesizing special polymers (U.S. Pat. No. 4,680,410).

U.S. Pat. No. 4,831,153 describes the synthesis of N-alkenylcarbamic esters by reacting the corresponding carbamic esters with acetaldehyde and thermolyzing the α-hydroxyalkyl compounds obtained in this way to give the N-alkenyl derivatives. One variant of this method is pyrolysis of the appropriate N-silyloxyalkyl precursors (U.S. Pat. No. 4,680,410).

These processes for preparing the N-alkenylcarbamic esters comprise two stages and require a thermal elimination step. They are thus relatively elaborate industrially and give only unsatisfactory overall yields because of losses of required product at the high reaction temperatures which are required.

U.S. Pat. No. 5,155,253 and EP-A 506 070 relate to processes for preparing N-alkenyl compounds from alkenyl esters and N-substituted carbamic esters in the presence of metals of the platinum group, especially ruthenium, as catalyst. In industrial processes, this involves reduction of the catalyst so that it is necessary to replenish the costly noble metal compounds.

It is an object of the present invention to provide a process which obviates said disadvantages of known processes.

We have found that this object is achieved by the above-defined process for preparing N-alkenylcarbamic esters of the formula I, wherein the starting compounds are reacted in the presence of a base.

The following equation illustrates the claimed process taking the example of the preparation of N-vinyloxazolidone from vinyl acetate and oxazolidone in the presence of 4-dimethylaminopyridine.

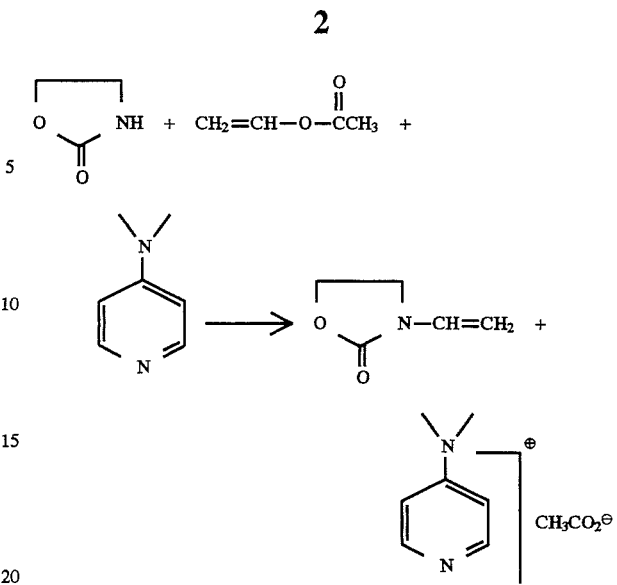

In the process according to the invenintion there is formal transfer of a vinyl group from a vinyl carboxylate of the formula II to a carbamic ester of the formula III.

The vinyl group of the esters of the formula II can carry a $C_1$-$C_4$—alkyl radical such as methyl, ethyl, n-propyl, isopropyl and n-butyl, but preferred compounds are those in which the $R^1$ radicals are hydrogen. The $R^4$ radical in the esters of the formula II takes the form of aliphatic radicals such as alkyl and alkenyl groups, which preferably have 1 to 40 carbon atoms and can be straight-chain or branched. $C_1$-$C_{20}$—Alkyl groups are particularly preferred, such as methyl, ethyl, n-propyl, n-butyl, tert-butyl, neodecyl and stearyl. $R^4$ can also take the form of cycloaliphatic radicals, preferably with 4–7 carbon atoms, eg. cyclopentyl and cyclohexyl. Aromatic radicals such as phenyl and naphthyl are also suitable, and these can carry substituents which are inert under the reaction conditions, such as halogen, alkoxy and alkyl. $R^4$ is also particularly preferably hydrogen.

Starting compounds of the formula II which may be mentioned are: vinyl formate, vinyl acetate, vinyl propionate, vinyl stearate, vinyl pivalate and vinyl 4-tert-butylbenzoate.

The compounds of the formula II are commercially available or can be prepared by known methods, for example by addition of carboxylic acids onto acetylene or by acetoxylation of ethylene (Weissermel and Arpe, Industrielle Organische Chemie, 2nd edition, 1978, Verlag Chemie, pages 217 et seq.).

The $R^2$ radical in the carbamic esters of the formula III takes the form of aliphatic radicals such as alkyl groups, which preferably have 1 to 10 carbon atoms and are straight-chain or branched. $C_1$-$C_4$—Alkyl groups are particularly preferred, such as methyl, ethyl, n-propyl and n-butyl.

$R^2$ can also be a cycloaliphatic radical such as cyclohexyl, an aromatic radical such as phenyl and an araliphatic radical such as benzyl. The $R^2$ radical can furthermore form with the $R^3$ radical a 2- to 10-membered bridge, with 2- to 7-membered alkylene bridges being preferred.

What has been said above concerning the $R^4$ radical applies similarly to the $R^3$ radical in the carbamic esters of the formula III, with the difference that $R^3$ is not hydrogen. Starting compounds which may be mentioned are: methyl N-methylcarbamate, methyl N-butylcarbamate, ethyl N-methylcarbamate, phenyl N-methylcarbamate, benzyl N-propylcarbamate and oxazolidone.

These compounds are also obtainable commercially or by known methods, eg. by reacting isocyanates with alcohols and reacting primary amines with alkyl chloroformates with elimination of HCl.

Preferred products are methyl N-butyl-N-vinylcarbamate and N-vinyloxazolidone.

The starting compounds are reacted in the presence of a base, preferably a Brönsted base. Suitable for this purpose are both inorganic and organic bases. These are, specifically, carbonates and bicarbonates of the alkali metals and alkaline earth metals, such as sodium carbonate, potassium carbonate and sodium bicarbonate, quaternary ammonium carbonates such as tetramethylammonium carbonate, amides such as alkali metal amides, for example sodium amide and potassium amide, hydroxides such as alkali metal hydroxides, for example lithium hydroxide, sodium hydroxide and potassium hydroxide, alkali metal carboxylates such as sodium acetate, alcoholates such as alkali metal alcoholates, for example sodium methanolate, sodium ethanolate, potassium methanolate and potassium tert-butanolate. Potassium hydroxide can also be used together with crown ethers such as 18-crown-6.

Further suitable bases are amines such as ammonia, primary, secondary and tertiary amines, of which the tertiary amines are preferred. The amines can carry aliphatic or aromatic radicals, for example trialkylamines such as trioctylamine, ethyldiisopropylamine, diethylisopropylamine, dimethylcyclohexylamine, triethylamine, also cyclic amines such as 2,2,6,6-tetramethylpiperidine, 1,4-diazabicyclo[2.2.2]octane, 1,8-diazabicyclo[5.4.0]undec-7-ene, amines carrying aliphatic and aromatic radicals, such as 1,8-bis(dimethylamino) naphthalene and 4-dimethylaminopyridine, and heterocyclic amines such as N-alkylimidazoles and N-arylimidazoles. Also suitable are amides such as dialkylformamides, eg. dibutylformamide. The process according to the invention can also be carried out in the presence of basic ion exchangers which, as a rule, consist of sulfonated styrene/divinylbenzene copolymers, such as Amberlite®, Lewatit® and Puralit®, and in the presence of basic zeolites such as hydrotalcite.

It is possible to use from 0.1 to 10, preferably 1 to 1.2, equivalents of the ester of the formula II per equivalent of carbamic ester of the formula III.

The amount of base can be from 0.1 to 3 equivalents, preferably 0.2 to 1 equivalent, per equivalent of carbamic ester of the formula III.

Although the reaction is preferably carried out without solvent, it is possible to add a solvent, eg. aprotic solvents such as ethers, eg. tetrahydrofuran, aromatic hydrocarbons such as toluene and xylene, ketones such as acetone, furthermore acetonitrile, hexamethylphosphoric triamide, sulfolane, dimethyl sulfoxide, ureas such as N,N'-dimethylethylene- and N,N'-dimethylpropyleneurea and tetrabutylurea. The amount is generally from 10 to 30% of the total weight of the mixture.

The reaction temperature is, as a rule, from 0° to 150° C., preferably 20° to 120° C. The reaction is preferably carried out under atmospheric pressure, but it is also possible to carry it out under from 0.01 to 10 bar.

The reaction can be carried out continuously or batchwise. Thus, the starting compounds and the base can be placed in a stirred vessel and reacted therein, in which case the sequence of addition of the individual components has no detectable effect on the reaction. It is also possible to react the starting compounds and the base in a tubular reactor with downward or upward flow. It has proven advantageous to carry out the reaction in a jet tube reactor.

The reaction is complete as a rule after 5 minutes to 8 hours.

The reaction mixture obtained in this way can be worked up in a conventional way. In general, the product is removed by distillation. The distillation residue can be treated with alkalis such as sodium hydroxide solution in order to liberate the organic bases from the salts produced in the reaction. The liberated bases can then be isolated by extraction or distillation. If volatile salt-like compounds, such as formates of tertiary ammonium compounds, are formed in the reaction according to the invention, these can also be worked up by distillation and converted into the corresponding amines. If 4-dimethylaminopyridine is used in the reaction according to the invention, the base can be recovered directly from the distillation residue by distillation. The bases which are separated off in each case can be returned to the reaction.

The process according to the invention permits N-alkenylcarbamic esters to be prepared in one stage from easily obtainable precursors. The reaction is simple to carry out industrially and takes place at mild reaction temperatures. Furthermore, it leads to a high yield of products.

EXAMPLES

Preparation of N-vinyloxazolidone

Example 1

43.5 g (0.5 mol) of oxazolidone were suspended in 100 ml of tetrahydrofuran, and 50 g (0.5 mol) of triethylamine were added. Then, at 70°–73° C., 52 g (0.6 mol) of vinyl acetate were added dropwise over the course of 30 minutes. After 5 h at 75° C., the reaction mixture was worked up by distillation.

Yield: 36.8 g (65%) of N-vinyloxazolidone

Example 2

As in Example 1, 43.5 g (0.5 mol) of oxazolidone were suspended in 100 g of xylene, and 61.1 g (0.5 mol) of 4-dimethylaminopyridine were added. Then 60 g (0.6 mol) of vinyl propionate were added dropwise at 105° C. over the course of 1 hour. After 5 hours at 110° C., the reaction mixture was worked up by distillation.

Yield: 46.9 g (83%) of N-vinyloxazolidone

Preparation of methyl N-butyl-N-vinylcarbamate

Example 3

22.4 g (0.2 mol) of methyl N-butylcarbamate were suspended in 50 g of xylene, and 12 g (0.1 mol) of 4-dimethylaminopyridine were added. The reaction mixture was then heated to 105° C., and 22 g (0.2 mol) of vinyl propionate were added dropwise over the course of 15 minutes. After 4 hours at 110° C., the reaction mixture was worked up by distillation.

Yield: 27.4 g (87%) of methyl N-butyl-N-vinylcarbamate

We claim:

1. A process for preparing N-alkenylcarbamic esters of the general formula I

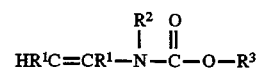

where at least one of the $R^1$ groups is hydrogen and the second $R^1$ group is hydrogen or $C_1$–$C_4$—alkyl, the $R^2$ group is an aliphatic, cycloaliphatic, araliphatic or aromatic group which can be linked to the $R^3$ group to form a 2- to 10-membered bridge, and the $R^3$ group is an aliphatic, cycloaliphatic or aromatic group, from an alkenyl carboxylate of the general formula II

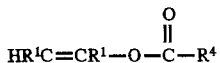

$$HR^1C{=}CR^1{-}O{-}\overset{\overset{O}{\|}}{C}{-}R^4 \quad \text{II}$$

where $R^1$ has the abovementioned meaning, and $R^4$ is hydrogen, an aliphatic, cycloaliphatic or aromatic group, and a carbamic ester of the general formula III

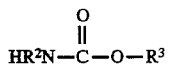

$$HR^2N{-}\overset{\overset{O}{\|}}{C}{-}O{-}R^3 \quad \text{III}$$

where the $R^2$ and $R^3$ groups have the abovementioned meanings, wherein the starting compounds are reacted in the presence of a base.

2. A process as claimed in claim 1, wherein the $R^1$ groups are hydrogen.

3. A process as claimed in claim 1, wherein the $R^2$ group is $C_1$-$C_{20}$—alkyl or forms with the $R^3$ group a 2- to 7-membered alkylene bridge.

4. A process as claimed in claim 1, wherein N-vinyloxazolidone or methyl N-vinyl-N-butylcarbamate is prepared.

5. A process as claimed in claim 1, wherein the reaction is carried out without solvent.

6. A process as claimed in claim 1, wherein 0.2 to 1 equivalent of base is used per equivalent of carbamic ester of the formula III.

7. A process as claimed in claim 1, wherein the reaction is carried out at 20° to 80° C.

8. A process as claimed in claim 1, wherein tertiary amines are used as base.

9. A process as claimed in claim 1, wherein sodium methoxide, potassium tert-butoxide or potassium carbonate is used as base.

* * * * *